United States Patent [19]
Schmidt et al.

[11] 4,047,929
[45] Sept. 13, 1977

[54] SYNERGISTIC HERBICIDAL COMPOSITIONS

[75] Inventors: Robert R. Schmidt, Cologne; Ludwig Eue, Leverkusen; Wilfried Draber, Wuppertal, all of Germany

[73] Assignee: Bayer Aktiengesellschaft, Leverkusen, Germany

[21] Appl. No.: 707,456

[22] Filed: July 21, 1976

[30] Foreign Application Priority Data
Aug. 21, 1975  Germany ............................. 2537290

[51] Int. Cl.$^2$ .............................................. A01N 9/22
[52] U.S. Cl. .......................................... 71/93; 71/108; 71/109; 71/116
[58] Field of Search ................................. 71/93, 108

[56] References Cited
U.S. PATENT DOCUMENTS

| | | | |
|---|---|---|---|
| 3,907,543 | 9/1975 | Dickore et al. | 71/93 |
| 3,910,909 | 10/1975 | Draber et al. | 71/93 |
| 3,954,442 | 5/1976 | Becker et al. | 71/108 |

FOREIGN PATENT DOCUMENTS

| | | | |
|---|---|---|---|
| 2,224,161 | 11/1973 | Germany | 71/93 |
| 2,413,262 | 9/1975 | Germany | 71/93 |

*Primary Examiner*—Joseph P. Brust
*Attorney, Agent, or Firm*—Burgess Dinklage & Sprung

[57] ABSTRACT

Herbicidal compositions containing (1) 3-methyl-4-amino-6-phenyl-1,2,4-triazin-5-one of the formula

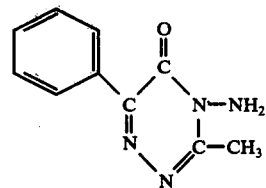

and (2) a 4-phenoxy-phenoxy-alkanecarboxylic acid derivative of the general formula

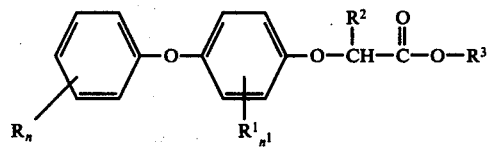

wherein
R and R$^1$ may be hydrogen or halogen
n and n$^1$ are integers from 1 to 3
R$^2$ is hydrogen or alkyl
R$^3$ is hydrogen or alkyl or a cation display outstanding synergistic effects when applied as herbicides.

10 Claims, No Drawings

SYNERGISTIC HERBICIDAL COMPOSITIONS

The present invention relates to new herbicidal combinations of a 3-alkyl-1,2,4-triazin-5-one and certain 4-phenoxy-phenoxy-alkane-carboxylic acid compounds.

It is known that 3-alkyl-1,2,4-triazin-5-ones, for example 3-methyl-4-amino-6-phenyl-1,2,4-triazin-5-one, can be used as selective herbicides in beets, from German Offenlegungsschrift (German Published Specification) No. 2,224,161, published on Nov. 29, 1973.

It is also known that 4-phenoxy-phenoxy-alkane-carboxylic acid derivatives can be used as herbicides, from German Offenlegungsschrift No. (German Published Specification) No. 2,223,894, published Dec. 13, 1973.

However, when using low amounts and low concentrations, the selective herbicidal activity of the above-mentioned materials is not always entirely satisfactory when combating weeds in beets.

The present invention provides a herbicidal composition containing as active ingredients (1) 3-methyl-4-amino-6-phenyl-1,2,4-triazin-5-one of the formula

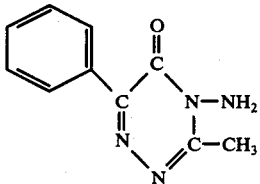

and (2) a 4-phenoxy-phenoxy-alkanecarboxylic acid derivative of the general formula

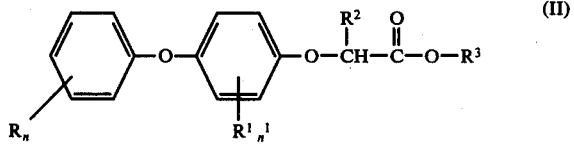

in which
R and $R^1$, which may be identical or different, each represent hydrogen or halogen,
n and $n^1$, which may be identical or different, each represent 1, 2 or 3,
$R^2$ represents hydrogen or alkyl with 1 to 4 carbon atoms and
$R^3$ represents hydrogen, alkyl with 1 to 4 carbon atoms,
an alkali metal cation or a dimethylammonium cation, alone or in admixture with a solid or liquid or liquefied gaseous diluent or carrier.

The active-compound combinations of this invention exhibit a particularly broad and selective herbicidal activity in beet cultures.

The present invention also provides a method of combating weeds which comprises applying to the weeds or a weed habitat a composition according to the present invention.

Preferably, in the formula (II), R and $R^1$, which may be identical or different, each represent hydrogen or chlorine, n is 1 or 2, $n^1$ is 1 or 2, $R^2$ represents methyl and $R^3$ represents hydrogen, methyl, ethyl or a sodium or potassium cation.

Surprisingly, the herbicidal activity of the active compound combinations according to the invention is substantially higher than the sum of the actions of the individual active compounds. Hence, one is dealing with an unforseeable genuine synergistic effect and not just a supplementary action. The active compound combinations are thus a valuable enrichment of beet herbicides.

The following may be mentioned as examples of compounds of the formula (II) which can be used according to the invention: 4-(2,4-dichlorophenoxy)-α-phenoxy-propionic acid, 4-(2,4-dichlorophenoxy)-α-phenoxy-propionic acid methyl ester, 4-(2,4-dichlorophenoxy)-α-phenoxy-propionic acid ethyl ester, the sodium salt of 4-(2,4-dichlorophenoxy)-α-phenoxy-propionic acid, the potassium salt of 4-(2,4-dichlorophenoxy)-α-phenoxy-propionic acid, 4-(4-chlorophenoxy)-α-phenoxy-propionic acid, 4-(4-chlorophenoxy)-α-phenoxy-propionic acid methyl ester, 4-(4-chlorophenoxy)-α-phenoxy-propionic acid ethyl ester and isobutyl ester, the sodium salt of 4-(4-chlorophenoxy)-α-phenoxy-propionic acid and the potassium salt of 4-(4chlorophenoxy)-α-phenoxy-propionic acid.

The active compounds contained in the active compound combinations according to the invention are already known (see German Offenlegungsschriften (German Published Specifications) Nos. 2,224,161 and 2,223,894).

The synergistic effect manifests itself particularly powerfully at certain concentration ratios. However, the weight ratios of the active compounds in the active compound combinations can vary within relatively broad ranges. In general, from 0.1 to 5 parts by weight, preferably from 0.1 to 3 parts by weight, of the active compound of the formula (II) are present per part by weight of active compound of the formula (I).

The active compound combinations according to the invention exhibit a very good action against weeds and wild grasses, without damaging the beets. They can therefore be used for the selective combating of weeds in beet cultures.

Relevant weeds are, in particular, dicotyledons such as mustard (Sinapis), cress (Lepidium), bed straw (Galium), chickweed (Stellaria), camomile (Matricaria), mayweed (Anthemis), gallant soldier (Galinsoga), goosefoot (Chenopodium) annual nettle (Urtica) groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), Lindernia, deadnettle (Lamium), speedwell (Veronica), mallow (Abutilon), emex (Emex), thornapple (Datura), violet (Viola), hemp-nettle (Galeopsis), poppy (Papaver) and knapweed (Centaurea), and monocotyledons such as barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum) quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadowfoxtail (Alopecurus) and silky bent-grass (Apera).

The good activity of the active compound combinations according to the invention against wild grasses which are difficult to combat, e.g. species of millet such as finger grass (Digitaria) and against weeds which are difficult to combat, e.g. cleavers (Galium aparine) should be singled out particularly. It is a special advantage that such wild grasses and weeds, which are usually difficult to combat, can be combated simultaneously with the active compound combinations according to the invention.

The active compound combinations according to the invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins and/or naphthenes, for example mineral oil fractions, non-phytotoxic vegetable oils, such as soy bean oil, linseed oil, rape-seed oil or olive-oil, alcohols, such as butanol or glycol as well as their ethers and esters, ketones, such as acetone, methyl, ethyl, ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active-compound combinations according to the invention can be present in the formulations as a mixture with other active compounds.

The formulations in general contain from 0.1 to 95 per cent by weight of the total active compounds, preferably from 0.5 to 90 per cent.

The active-compound combinations can be used as such, in the form of their formulations or as the use forms prepared therefrom, such as ready-to-use solutions, emulsions, foams, suspensions, powders, pastes and granules. They are used in the customary manner, for example by dusting, atomising, spraying, watering and scattering.

The amounts used of the active-compound combinations according to the invention can be varied within a wide range. In general, they are between 0.5 and 20 kg/ha, preferably between 2 and 15 kg/ha.

The active-compound combinations according to the invention can be used before and/or after the emergence of the plants. Preferably, they are used after the emergence of the plants.

The present invention further provides means of yielding crops protected from damage by weeds by being grown in areas in which immediately prior to and/or during the time of the growing a composition according to the present invention was applied. It will be seen that the usual method of providing a harvested crop may be improved by the present invention.

The good herbicidal action of the active-compound combinations can be seen from the biotest Example which follows. Although the individual active compounds show shortcomings in herbicidal action, the combination shows a very broad action against weeds, which exceeds a simple summation of the actions.

A synergistic effect exists with herbicides whenever the herbicidal action of the active compound combination is greater than that of the individually applied active compounds.

The expected action of a given combination of two herbicides can be calculated as follows (see Colby, S. R., "Calculating synergistic and antagonistic responses of herbicide combinations", Weeds 15, pages 20–22, 1967): If $X = \%$ damage by herbicide A when using $p$ kg/ha and $Y = \%$ damage by herbicide B when using $q$ kg/ha and $E = $ the expected damage by herbicides A and B when using $p$ and $q$ kg/ha, then $E = X + Y - (X \cdot Y/100)$.

If the actual damage is greater than calculated, the action of the combination is super-additive, that is to say a synergistic effect exists.

The table in Example A unambiguously shows that the found herbicidal action of the active compound combination according to the invention on weeds is greater than the calculated action, that is to say a genuine synergistic effect exists.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. The concentrations of the spray liquor was so chosen that the amounts of active compound shown in the table were applied in 2,000 l of water/ha. After 3 weeks, the degree of damage to the plants was rated in % damage in comparison to the development of the untreated control. The figures denote:

0% = no action (like untreated control)
100% = total destruction.

The active compounds, the amounts applied and the results can be seen from the table which follows:

Table A

| Active compound or active compound combination | Post-emergence test Amount of active compound used kg/ha | Beets found* | Beets calc.* | Digitaria spec. found* | Digitaria spec. calc.* | Poa annua found* | Poa annua calc.* | Galium aparine found* | Galium aparine calc.* |
|---|---|---|---|---|---|---|---|---|---|
| 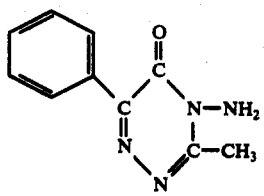 (known) (I) | 3 | 0 | | 30 | | 80 | | 100 | |
| | 1.5 | 0 | | 10 | | 50 | | 80 | |
| 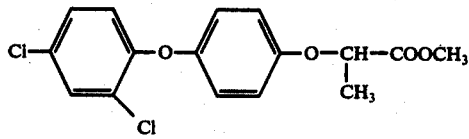 (known) (II-1) | 1.5 | 20 | | 80 | | 30 | | 0 | |
| (I) + (II-1) (according to the invention) | 1.5 + 1.5 | 0 | 20 | 100 | 82 | 90 | 65 | 100 | 80 |
| | 3.0 + 1.5 | 0 | 20 | 100 | 86 | 95 | 86 | 100 | 100 |

*found = damage found
*calc. = damage calculated in accordance with the formula given earlier It will be understood that the specification and examples are illustrative but not limitative of the present invention and that other embodiments within the spirit and scope of the invention will suggest themselves to those skilled in the art.

What is claimed is:

1. A herbicidal composition containing as active ingredients, in herbicidally effective amounts, (1) 3-methyl-4-amino-6-phenyl-1,2,4-triazin-5-one of the formula

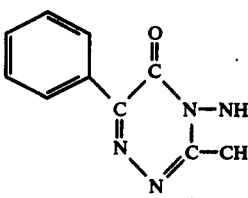

and (2) a 4-phenoxy-phenoxy-alkanecarboxylic acid of the formula

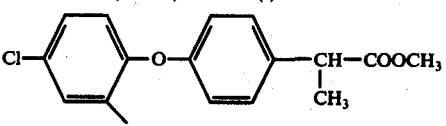

wherein the weight ratio of compound (1) to compound (2) is from about 1:1 to about 2:1.

2. A herbicidal composition as claimed in claim 1 wherein the weight ratio of the active compound of the formula (I) to active compound of the formula (II) is about 1:1

3. A herbicidal composition as claimed in claim 1 wherein the weight ratio of the active compound of the formula (I) to active compound of the formula (II) is about 2:1.

4. A herbicidal composition as claimed in claim 1 containing from 0.1 to 95% of the total active compounds, by weight.

5. A herbicidal composition as claimed in claim 4 containing from 0.5 to 90% of the total active compounds, by weight.

6. A herbicidal composition as claimed in claim 1 also comprising an agriculturally acceptable carrier, especially a carrier containing a surface active agent or a non-phytotoxic oil.

7. A method of combating weeds which comprises applying to the weeds or a weed habitat a herbicidal composition as claimed in claim 1.

8. A method as claimed in claim 7 wherein the active compounds are applied to an area of agriculture in an amount of 0.5 to 20 kg of total active ingredients per hectare.

9. A method as claimed in claim 8 wherein the active compounds are applied in an amount of from 2 to 15 kg of total active ingredients per hectare.

10. A method as claimed in claim 7 wherein the composition is applied to an area of beet cultivation.

* * * * *